(12) United States Patent
Parthasarathy et al.

(10) Patent No.: US 10,376,179 B2
(45) Date of Patent: Aug. 13, 2019

(54) MPR SLICE SELECTION FOR VISUALIZATION OF CATHETER IN THREE-DIMENSIONAL ULTRASOUND

(75) Inventors: Vijay Parthasarathy, Tarrytown, NY (US); Ameet Kumar Jain, New York, NY (US); Charles Ray Hatt, III, Madison, WI (US); Amish N. Raval, Middleton, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1211 days.

(21) Appl. No.: 14/113,035

(22) PCT Filed: Apr. 19, 2012

(86) PCT No.: PCT/IB2012/051974
§ 371 (c)(1),
(2), (4) Date: Mar. 10, 2014

(87) PCT Pub. No.: WO2012/143885
PCT Pub. Date: Oct. 26, 2012

(65) Prior Publication Data
US 2014/0187919 A1    Jul. 3, 2014

Related U.S. Application Data

(60) Provisional application No. 61/477,659, filed on Apr. 21, 2011.

(51) Int. Cl.
*A61B 5/05* (2006.01)
*A61B 5/06* (2006.01)
(Continued)

(52) U.S. Cl.
CPC ........... *A61B 5/062* (2013.01); *A61B 6/12* (2013.01); *A61B 6/503* (2013.01); *A61B 8/0841* (2013.01);
(Continued)

(58) Field of Classification Search
USPC ........................................... 600/424
See application file for complete search history.

(56) References Cited

U.S. PATENT DOCUMENTS 6,064,904 A * 5/2000 Yanof ............... A61B 19/20
600/414
6,741,883 B2   5/2004 Gildenberg
(Continued)

FOREIGN PATENT DOCUMENTS

WO    WO2012073165    6/2012

OTHER PUBLICATIONS

L.F. Gutierrez et al., "Multimodality Image Guidance system Integrating X-Ray Fluoroscopy and Ultrasound Image Streams With Electromagnetic Tracking", Medical Imaging 2007: Visualization and Image-Guided Procedures, Proc. of SPIE vol. 6509, 65090K-1 through 65090K-10, (2007).

*Primary Examiner* — Joel F Brutus
(74) *Attorney, Agent, or Firm* — Sherry Austin (57) ABSTRACT

A system employs an interventional tool (30), ultrasound imaging system and a multi-planar reformatting module (40). The interventional tool (30) has one or more image tracking points (31). The ultrasound imaging system includes an ultrasound probe (20) operable for generating an ultrasound volume image (22) of a portion or an entirety of the interventional tool (30) within an anatomical region. The multi-planar reformatting imaging module (40) generates two or more multi-planar reformatting images (41) of the interventional tool (30) within the anatomical region. A generation of the two multi-planar reformatting images (41) includes an identification of each image tracking point (31) within the ultrasound volume image (22), and a utilization of each identified image tracking point (31) as an origin of the multi-planar reformatting images (41).

20 Claims, 10 Drawing Sheets

(51) Int. Cl.
*A61B 8/08* (2006.01)
*A61B 6/12* (2006.01)
*A61B 6/00* (2006.01)
*A61B 8/00* (2006.01)
*G06T 15/08* (2011.01)
*A61M 25/01* (2006.01)
*A61B 34/20* (2016.01)
*A61B 17/00* (2006.01)
*A61B 90/00* (2016.01)

(52) U.S. Cl.
CPC ............ *A61B 8/4254* (2013.01); *A61B 8/466* (2013.01); *A61B 8/483* (2013.01); *A61B 8/523* (2013.01); *A61B 8/5261* (2013.01); *A61B 34/20* (2016.02); *A61M 25/0108* (2013.01); *A61M 25/0127* (2013.01); *G06T 15/08* (2013.01); *A61B 6/5247* (2013.01); *A61B 8/0883* (2013.01); *A61B 2017/00243* (2013.01); *A61B 2017/00703* (2013.01); *A61B 2034/2051* (2016.02); *A61B 2034/2061* (2016.02); *A61B 2034/2065* (2016.02); *A61B 2090/367* (2016.02); *A61B 2090/376* (2016.02); *A61B 2090/378* (2016.02); *G06T 2210/41* (2013.01)

(56) References Cited

U.S. PATENT DOCUMENTS

| | | | |
|---|---|---|---|
| 7,346,381 | B2 | 3/2008 | Okerlund et al. |
| 8,126,239 | B2 | 2/2012 | Sun et al. |
| 8,303,502 | B2 | 11/2012 | Washburn et al. |
| 8,731,264 | B2 | 5/2014 | Kruecker et al. |
| 2004/0106869 | A1* | 6/2004 | Tepper ............... A61B 8/0833 600/443 |
| 2005/0245803 | A1* | 11/2005 | Glenn, Jr. ........... A61B 5/4255 600/407 |
| 2006/0020204 | A1 | 1/2006 | Serra et al. |
| 2006/0193504 | A1 | 8/2006 | Salgo et al. |
| 2007/0167806 | A1* | 7/2007 | Wood ................... A61B 6/032 600/459 |
| 2008/0009722 | A1* | 1/2008 | Simopoulos ........... A61B 8/08 600/437 |
| 2008/0095421 | A1* | 4/2008 | Sun ..................... A61B 6/12 382/131 |
| 2009/0088628 | A1 | 4/2009 | Klingenbeck-Regn |
| 2009/0118609 | A1 | 5/2009 | Rahn |
| 2009/0136106 | A1* | 5/2009 | Roberts ............... G06T 15/08 382/130 |
| 2009/0274271 | A1 | 11/2009 | Pfister et al. |
| 2010/0056560 | A1 | 3/2010 | Park et al. |
| 2010/0081920 | A1* | 4/2010 | Whitmore, III ..... A61B 8/4254 600/424 |
| 2010/0254583 | A1 | 10/2010 | Chan et al. |
| 2010/0268085 | A1 | 10/2010 | Kruecker et al. |
| 2011/0160588 | A1 | 6/2011 | Ichikawa |

* cited by examiner

MPR SLICE SELECTION FOR VISUALIZATION OF CATHETER IN THREE-DIMENSIONAL ULTRASOUND

CROSS-REFERENCE TO PRIOR APPLICATIONS

This application is the U.S. National Phase application under 35 U.S.C. § 371 of International Application Serial No. PCT/IB2012/051974, filed on Apr. 19, 2012, which claims the benefit of U.S. Application Ser. No. 61/477,659, filed on Apr. 21, 2011. These applications are hereby incorporated by reference herein.

The present invention generally relates to accurate visualization of an interventional tool during an interventional procedure, particularly an accurate visualization of a catheter during an interventional cardiac procedure. The present invention specifically relates to the visualization of the interventional tool in multi-planar reformatting ("MPR") images derived from a three-dimensional ultrasound image ("3D US").

Knowing a relative position of an interventional tool (e.g., a catheter) with respect to a pre-procedural planning scan (e.g., a magnetic resonance imaging ("MRI") scan or a computed tomography ("CT") scan) is important for accurate guidance in an interventional procedure, particularly an interventional cardiac procedure. Since X-ray fluoroscopic images provide very highly resolved images of the interventional tool during the procedure, image-guided systems known in the art for providing visual aid in guiding the interventional tool have concentrated on tracking a tip of the tool in fluoroscopic images and overlaying in the pre-procedural scan.

Increasingly, registering an ultrasound image ("2D US") or 3D US with X-ray imaging has augmented X-ray fluoroscopy as an aid for guiding an interventional procedure. The key role of the 2D US or the 3D US is to augment the pre-procedural scan with real time motion information, while the X-ray fluoroscopic image(s) provide high resolution visualization of the interventional tool in real time. Moreover, with the introduction of 3D US in real time, it is becoming possible to visualize the interventional tool more clearly in ultrasound, thereby enabling ultrasound-only guided interventions.

Localization of the tip of the interventional tool is of paramount importance for accurate navigation and targeting. In particular, for cardiovascular interventions, the visualization of the relationship of a tip and a body of the catheter with respect to the surrounding tissue is important for accurate navigation and targeting. However, visualization of the exact location and orientation of a tip and a body of an interventional tool is often difficult in 2D US or 3D US due to (1) image artifacts from the body of the interventional tool, (2) a limited view of 2D US or 3D US, and (3) out of plane issues involving the tip of the interventional tool going in and out of the 2D US image or 3D US image.

With the difficulty in visualizing the tip of the interventional device in 3D US, it is also difficult to define multi-planar reformatting ("MPR") views around the tip of the interventional device whereby the neighborhood of the tool tip including surrounding tissue is appropriately visualized.

The present invention provides systems and methods for accurate real-time localizing of a tool tip in 3D US and for precise generation of the MPR views of the tool tip and surrounding neighborhood.

One form of the present invention is a system employing an interventional tool, ultrasound imaging system and a MPR imaging device. The interventional tool has one or more image tracking points (e.g., a catheter having an image tracking point located within a tip area of the catheter). The ultrasound imaging system including an ultrasound probe operable for generating an ultrasound volume image of a portion or an entirety of the interventional tool within an anatomical region. The MPR imaging module generates two or more multi-planar reformatting images of the interventional tool within the anatomical region. A generation of the multi-planar reformatting images includes an identification of each image tracking point within the ultrasound volume image, and a utilization of each identified image tracking point as an origin of one of the multi-planar reformatting images.

A second form of the present invention is a method involving a navigation of an interventional tool within an anatomical region, the interventional tool having one or more image tracking points (e.g., a catheter having an image tracking point located within a tip area of the catheter). The method further involves an operation of an ultrasound probe to generate an ultrasound volume image of a portion or an entirety of the interventional tool within the anatomical region, and an operation of a MPR imaging module to generate two or more multi-planar reformatting images of the interventional tool within the anatomical region. The generation of multi-planar reformatting images includes an identification of each image tracking point within the ultrasound volume image, and a utilization of each identified image tracking point as an origin of one of the multi-planar reformatting images.

The foregoing forms and other forms of the present invention as well as various features and advantages of the present invention will become further apparent from the following detailed description of various exemplary embodiments of the present invention read in conjunction with the accompanying drawings. The detailed description and drawings are merely illustrative of the present invention rather than limiting, the scope of the present invention being defined by the appended claims and equivalents thereof.

As previously stated, the present invention provides various systems and methods for visualizing a tool tip and surrounding neighborhood within MPR images derived from a 3D US image. As will be appreciated by those having ordinary skill in the art from the following descriptions of FIGS. 1-14, these methods are implemented by a MPR imaging module of the present invention.

Figure 1:
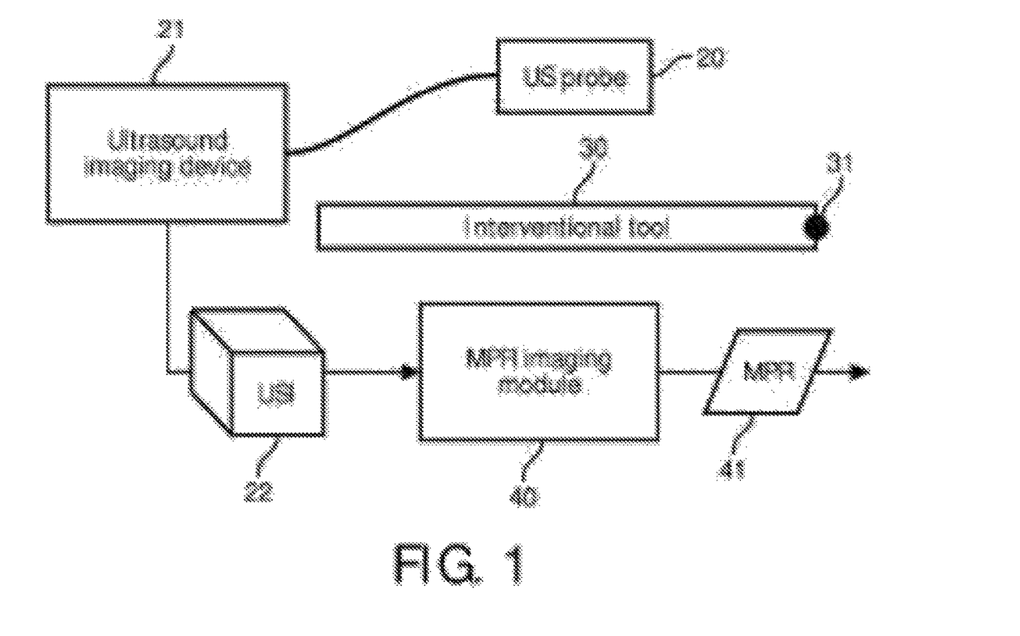
FIG. 1 illustrates an exemplary embodiment of an interventional tracking system in accordance with present invention.

FIG. 1 illustrates a system of the present invention employing 3D ultrasound imaging system, an interventional tool 30 and a MPR imaging device 40.

For purposes of the present invention, the 3D US imaging system is broadly defined herein as including a 3D US imaging device 21 for controlling an operation of 3D US probe 20 structurally configured for generating an ultrasound volume image ("USI") 22 of an anatomical region (e.g., cardiac region of a body). Examples of the 3D US imaging system include, but are not limited to, any type of 3D ultrasound imaging system utilizing a 3D TEE probe. In one embodiment, the iE33 intelligent echo system commercially sold by Philips Healthcare may serve as the 3D US imaging system.

For purposes of the present invention, interventional tool 30 is broadly defined herein as any type of tool, instrument or device structurally configured for performing specific actions of carrying out desired effects during any type of interventional procedure (e.g., interventional cardiology). For purposes of an interventional procedure, one or more image tracking points 31 are defined on the tip area or body of interventional device 30. In one embodiment, the tracking point is a tip of interventional device 30. In a second embodiment, each image tracking point 31 is defined by a sensor located in the tip area and/or body of interventional device 30. Examples of the sensor include, but are not limited to, an electromagnetic sensor, an optical sensor or a shape tracking sensor (e.g., a sensor making use of Fiber-Bragg gratings, Rayleigh scattering, backscattering, force sensing using optical fibers or measurement of deformities in optical fiber to track shape or location).

For purposes of the present invention, MPR imaging module 40 is broadly defined herein as any structural configuration of hardware, software and/or firmware for generating a MPR image 41 from ultrasound volume image 22 whereby an imaging tracking point 31 of interventional tool 30 serves as an origin of MPR image 41. In practice, MPR image 41 may have any orientation relative to the imaging tracking point 31 and may have any orientation within ultrasound volume image 22. Also in practice, MPR imaging module 40 may be integrated within ultrasound imaging device 21 or any other type of imaging or display device suitable for an interventional procedure.

To facilitate an understanding of MPR imaging module 40, a description and exemplarily implementation of an interventional tracking method of the present invention will now be described herein.

Figure 2:
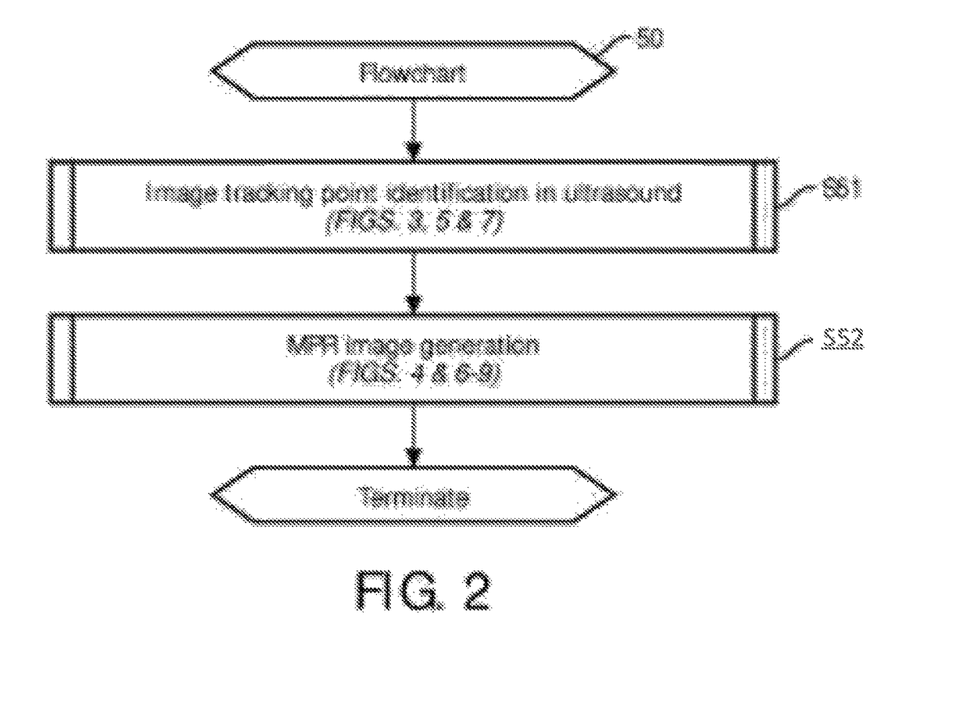
FIG. 2 illustrates a flowchart representative of an interventional tracking method in accordance with the present invention.

FIG. 2 illustrates a flowchart 50 representative of the interventional tracking method of the present invention. A stage S51 of flowchart 50 encompasses an identification of one or more image tracking points 31 of interventional tool 30 within ultrasound volume image 22, and a stage S52 of flowchart 50 encompasses a generation of one or more MPR images 41 with each identified image tracking point 31 serving as an origin of one of the MPR images 41.

Figure 3:
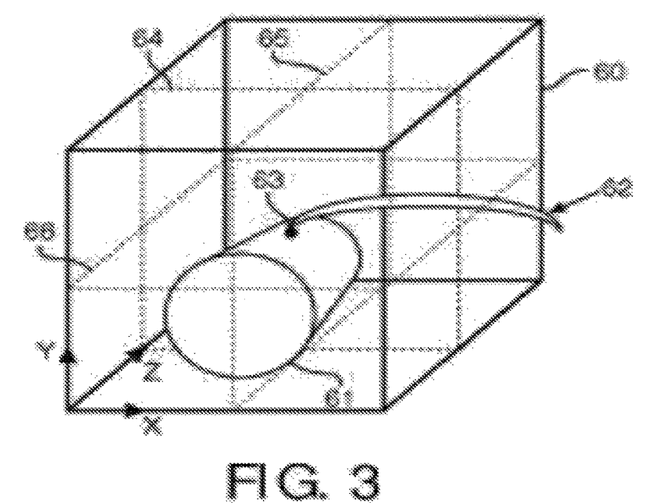
FIGS. 3 and 4A-C illustrate a first exemplary implementation of the interventional method of FIG. 2 by the interventional tracking system of FIG. 1.
Figure 4A:
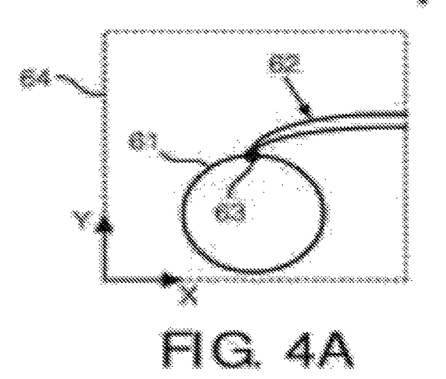
Figure 4B:
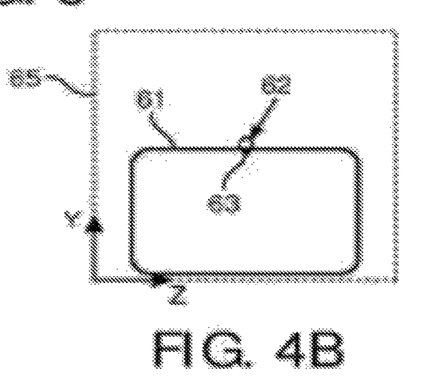
Figure 4C:
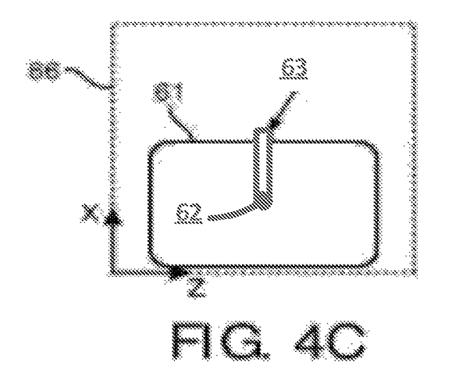

For example, FIG. 3 shows an identification of a tip 63 of an interventional tool 62 within an ultrasound volume image 60 of an anatomical region including tissue 61, and the identified tip 63 serves as an origin of orthogonal MPR images 64-66 as shown in respective FIGS. 4A-4C. As a result, tip 63 of interventional tool 62 as well as neighboring portions of tissue 61 are accurately visualized in MPR images 64-66.

During the interventional procedure, MPR images 64-66 are continually updated as interventional tool 62 is navigated within the anatomical region and/or the ultrasound probe is moved relative to the anatomical region. To maintain an accurate visualization of tip 63 and neighboring portions of tissue 61, MPR image 64 has a fixed parallel relationship with plane XY of ultrasound volume image 60, MPR image 65 has a fixed parallel relationship with plane YZ of ultrasound volume image 60 and MPR image 66 has a fixed parallel relationship with plane XZ of ultrasound volume image 60.

Figure 5:
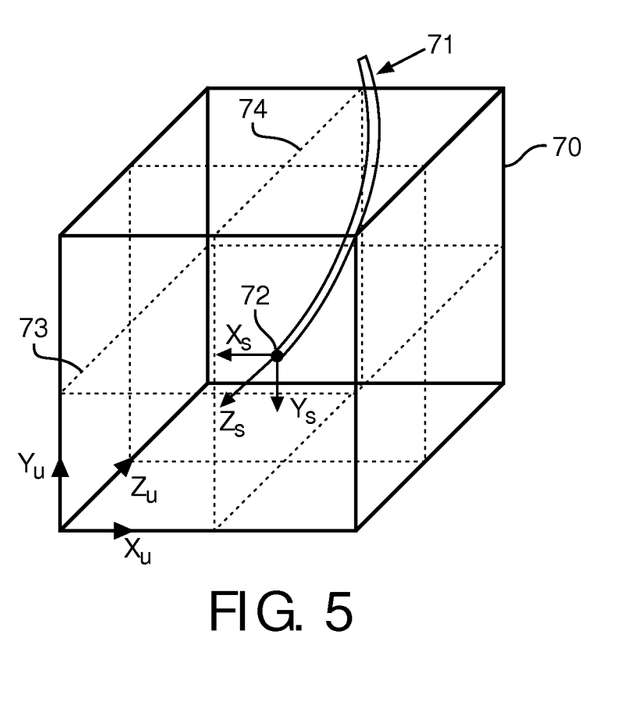
FIGS. 5 and 6A-B illustrate a second exemplary implementation of the interventional method of FIG. 2 by the interventional tracking system of FIG. 1.
Figure 6A:
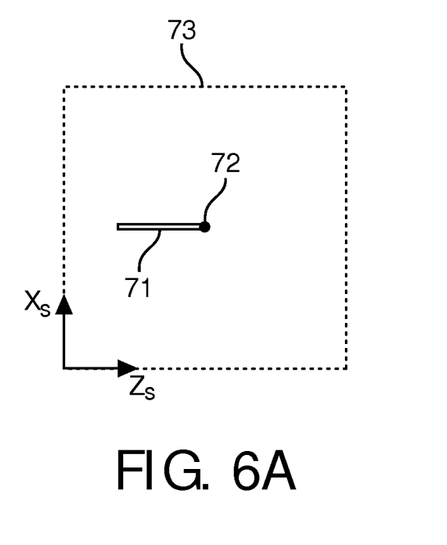
Figure 6B:
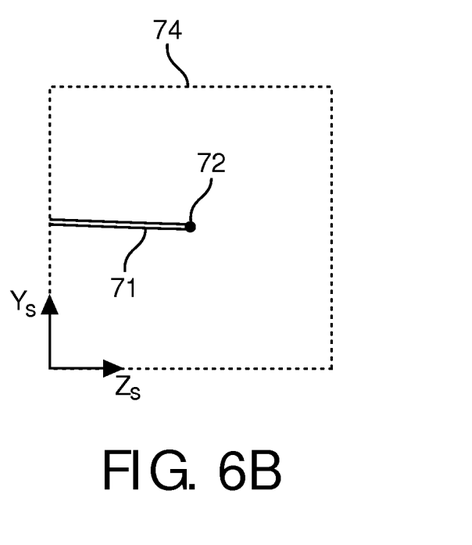

By further example, FIG. 5 shows an identification of an electromagnetic sensor 72 of an interventional tool 71 within an ultrasound volume image 70 of an anatomical region and the identified sensor 72 serves as an origin of MPR images 73 and 74 as shown in respective FIGS. 6A and 6B. Electromagnetic sensor 72 is located within a tip section of interventional tool 71. As a result, the tip of interventional tool 71 as well as neighboring portions of any tissue within the anatomical region are accurately visualized in MPR images 73 and 74. Please note tissue is not shown in FIG. 5 for purposes of illustrating sensor coordinate system $X_S Y_S Z_S$.

During the interventional procedure, MPR images 73 and 74 are continually updated as interventional tool 71 is navigated within the anatomical region and/or the ultrasound probe is moved relative to the anatomical region. To maintain an accurate visualization of the tip of interventional tool 71 and neighboring portions of tissue, MPR image 73 has a fixed parallel relationship with plane $X_s Z_s$ of the sensor coordinate system and MPR image 74 has a fixed parallel relationship with plane $Y_s Z_s$ of the sensor coordinate system.

Figure 7:
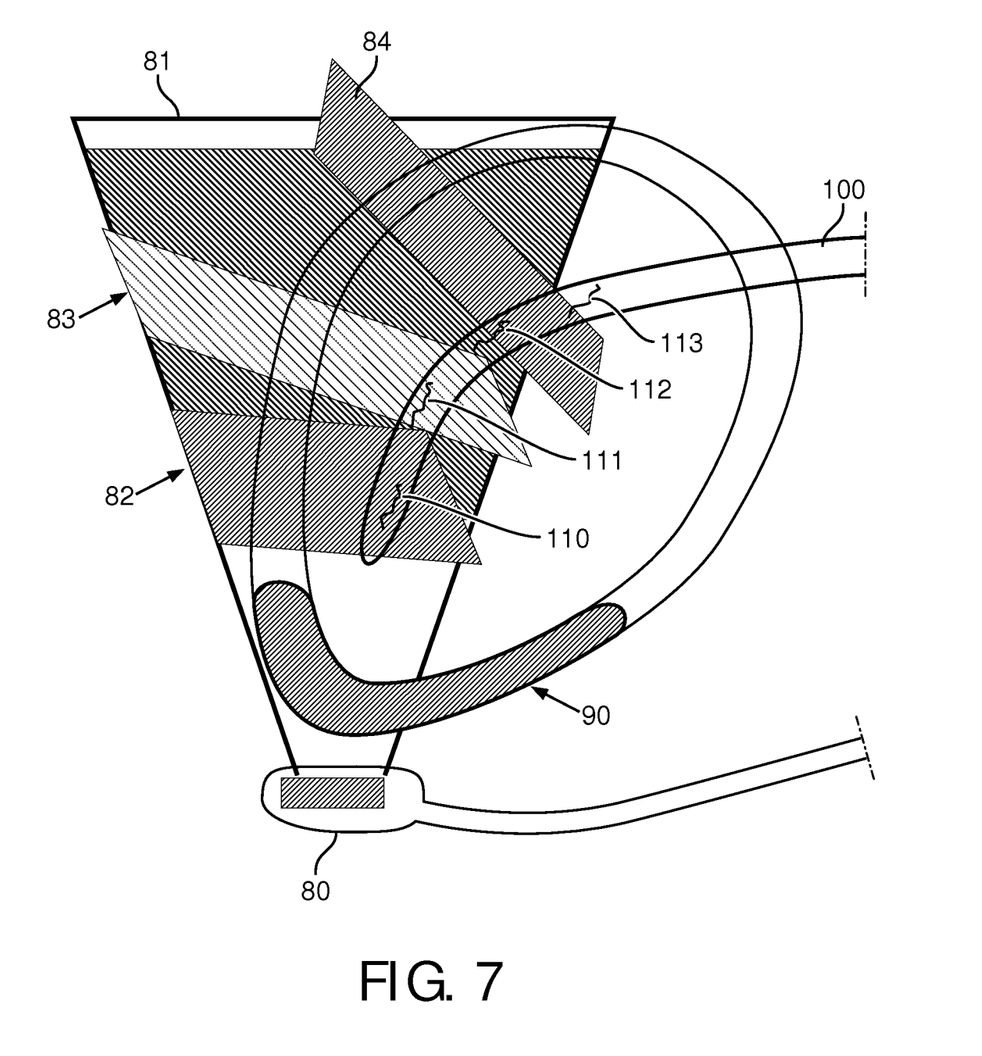
FIGS. 7-9 illustrate a second exemplary implementation of the interventional method of FIG. 2 by the interventional tracking system of FIG. 1.

By further example, FIG. 7 illustrates an ultrasound probe 80 generating an ultrasound volume image 81 relative to an infarct region 90 of a heart. An interventional tool 100 has a defined spacing of electromagnetic sensors 110-113 relative to a tip of interventional tool 100. Three (3) MPR images 82-84 are generated with respective sensors 110-112 serving as the origin of MPR images 82-84 with each MPR image 82-84 being normal to the respective sensors 110-112.

Figure 8:
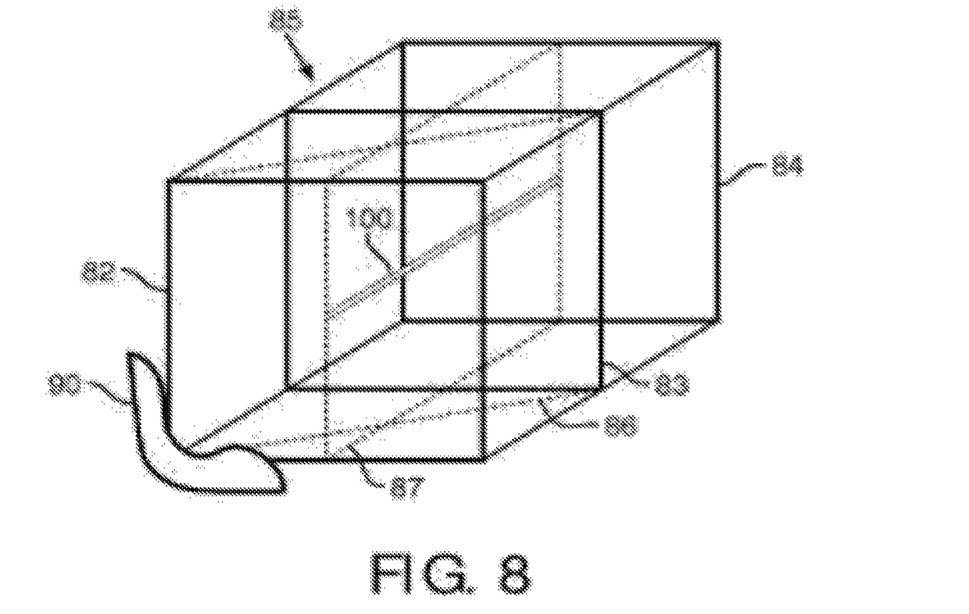

To visualize both the tip and the body of interventional tool 100, MPR images 82-84 are arranged in a stack formation whereby interventional tool 100 is axially aligned. For instances whereby interventional tool 100 has a non-linear orientation within ultrasound volume image 81, the stacking of MPR images 82-84 warps ultrasound volume image 81 into an ultrasound volume image 85 as shown in FIG. 8. Ultrasound volume image 85 represents a centric rectangular shape having a dynamic frame of reference with tool 100 as its axis and the tip of tool 100 on one of its edges. As such, in practice, ultrasound volume image 85 may be utilized for various purposes.

In one embodiment, ultrasound volume image 85 may be resliced into one or more arbitrary MPR images containing a portion of the body of interventional tool 100, such as, for example MPR images 86 and 87 as shown in FIG. 8. This reslicing of ultrasound volume image 85 provides real-time soft tissue context around the body of interventional tool 100.

In a second embodiment, a target volume may be segmented from a pre-operative scan and then overlaid on ultrasound volume image 85 to aid in targeting the volume.

Figure 9:
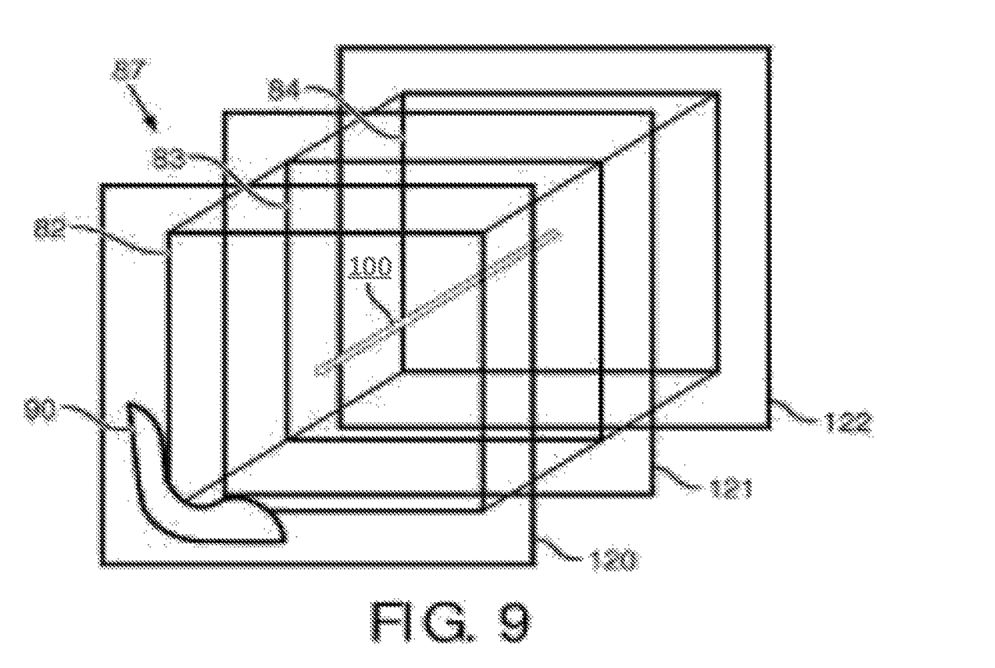

In a third embodiment, a pre-operative or an intra-operative scan (e.g., a MRI scan or a CT scan) from an imaging modality registered with electromagnetic frame of reference may be fused with ultrasound volume image 85, such as, for example, a fusion 87 of scan images 120-122 with MPR images 82-84 as shown in FIG. 9.

In a fourth embodiment, instead of showing the entire ultrasound image volume 85 within the scan fusion 87, only the axis of ultrasound volume image 85 may be visualized along with a target volume rendered in the space of the ultrasound volume image 85. This will hide the ultrasound data, but use the ultrasound data in the background to move the target volume in real-time.

To further facilitate an understanding of MPR imaging module 40, a description and exemplarily implementation of various interventional tracking systems of the present invention will now be described herein.

Figure 10:
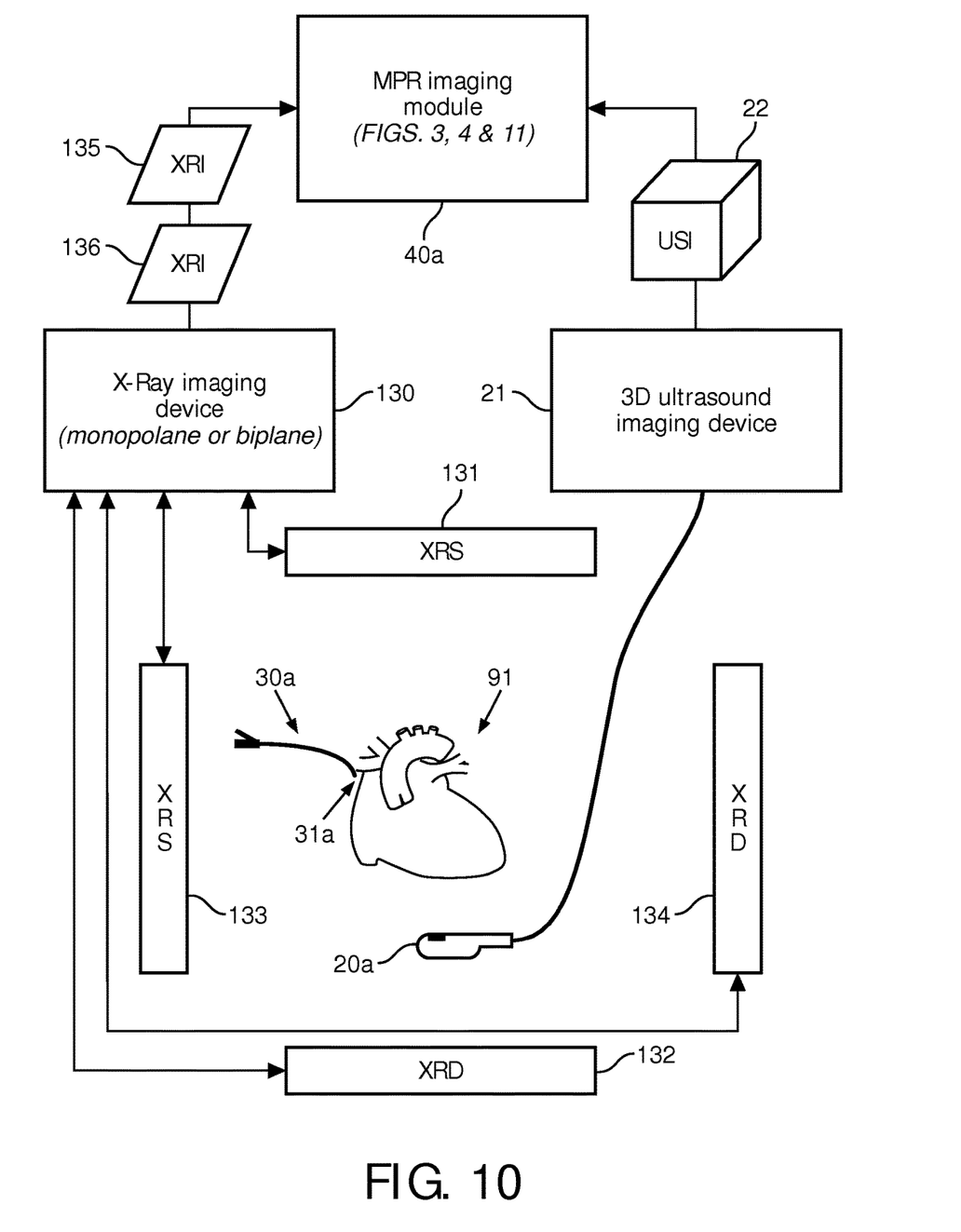
FIG. 10 illustrates a first exemplary embodiment of the interventional tracking system of FIG. 1.

FIG. 10 illustrates an interventional tracking system employing an X-ray imaging system, an embodiment of 3D US imaging system of FIG. 1 and an embodiment of MPR imaging device 40 of FIG. 1.

For purposes of the present invention, the X-ray imaging system is broadly defined herein as including an X-ray imaging device 130 for controlling an operation of an X-ray source 131 and an X-ray detector 132 structurally configured for generating a X-ray image ("XRI") 135 of an anatomical region (e.g., a cardiac region) represented by a volume and/or for controlling an operation of an X-ray source 133 and an X-ray detector 134 structurally configured for generating a X-ray image ("XRI") 136 of anatomical region 91. In practice, components 130-132 exclusive of components 133 and 134 represent a monoplane X-ray system of any type, and components 130-134 collectively represent a bi-plane X-ray system of any type. Examples of the X-ray imaging system include, but are not limited to, any type of X-ray system for performing a cardiac interventional procedure. In one embodiment, an X-ray system from the Allure Xper series commercially sold by Philips Medical Systems may serve as the X-ray imaging system.

Figure 11:
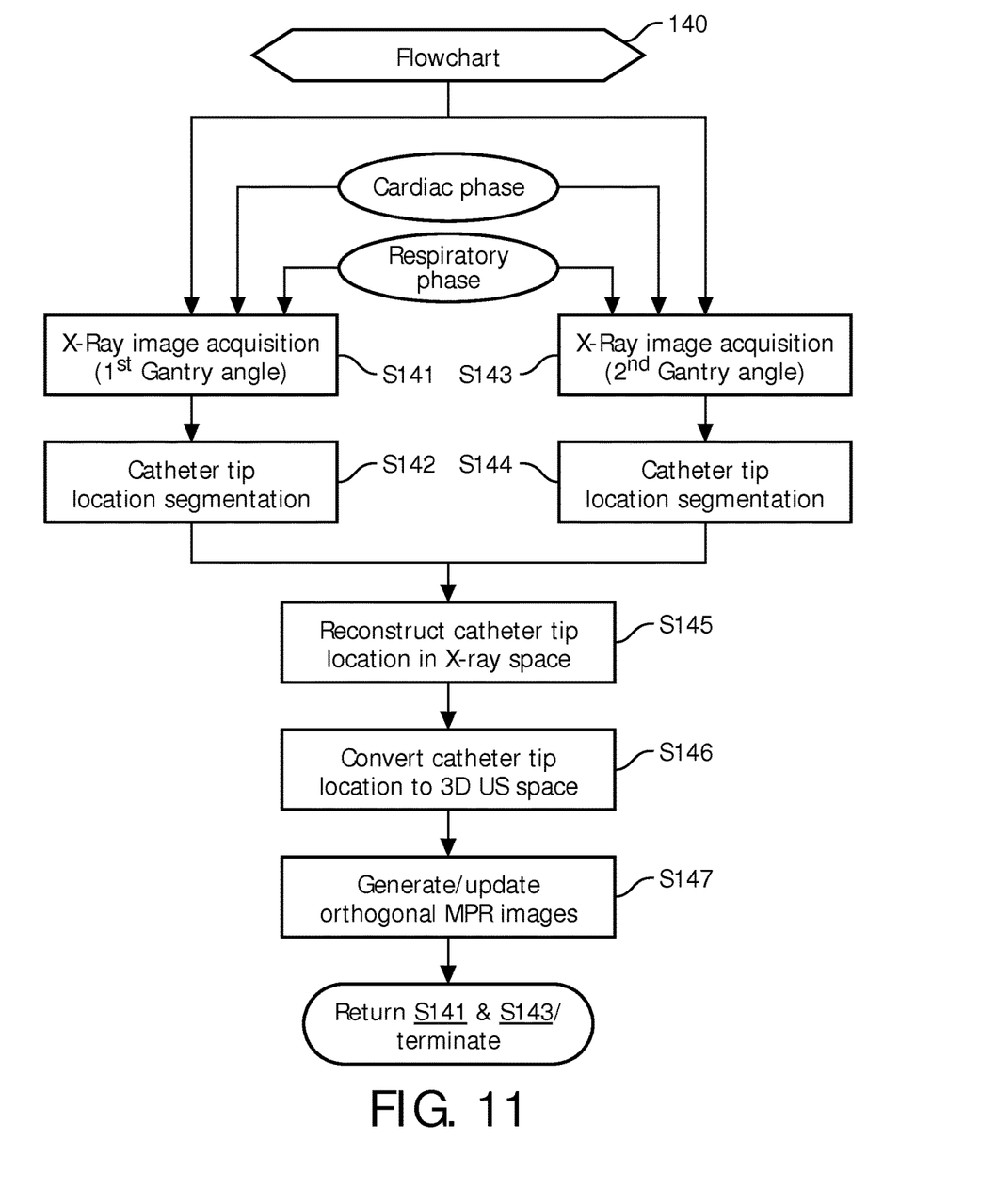
FIG. 11 illustrates a first exemplary embodiment of the interventional tracking method of FIG. 2.

In operation, an interventional tracking method represented by a flowchart 140 shown in FIG. 11 is executed for purposes of generating MPR images of a portion or an entirety of a catheter 30a within a cardiac anatomical region 91 as derived from an ultrasound volume image 22 and X-ray images 135 and 136.

Specifically, referring to FIGS. 10 and 11, upon a catheter 30a being inserted within a cardiac anatomical region 91, a stage S141 of flowchart 140 encompasses an X-ray image acquisition by X-Ray imaging device 130 of catheter 30a at a 1st gantry angle during a specified cardiac phase (e.g., an end diastole phase) and a specified respiratory phase (e.g., an end respiratory phase) using known cardiac and respiratory gating techniques, and a stage S142 of flowchart 140 encompasses a manual or automatic segmentation by MPR imaging module 40a of a catheter tip 31a in the X-ray image acquired during stage S141.

For a monoplane X-ray imaging system, a stage S143 of flowchart 140 encompasses an X-ray image acquisition by X-Ray imaging device 130 of catheter 30a at a 2nd gantry angle during the same specified cardiac phase and the same specified respiratory phase using known cardiac and respiratory gating techniques, and a stage S144 of flowchart 140 encompasses a manual or automatic segmentation by MPR imaging module 40a of catheter tip 31a in the X-ray image acquired during stage S143.

For a biplane X-ray imaging system, stages S141/S142 and stages S143/S144 may be executed simultaneously.

For either X-ray imaging system, a corresponding 3D location of catheter tip 31a in the 2D X-ray coordinate system is reconstructed by MPR imaging module 40a during a stage S145 of flowchart 140. In one embodiment of stage S145, a known epipolar constraint is utilized to reconstruct the 3D location of catheter tip 31a in the 2D X-ray coordinate system.

Thereafter, during a stage S146 of flowchart 140, a reconstructed 2D X-ray coordinate location of catheter tip 31a is converted into a 3D US real-time coordinate location by MPR imaging module 40a using system calibration and real-time tracking In one embodiment of stage S146, a manual alignment is used as the basis for the conversion. In a second embodiment of stage S146, a known electromagnetic tracking technique is used as the basis for the conversion.

Figure 12:
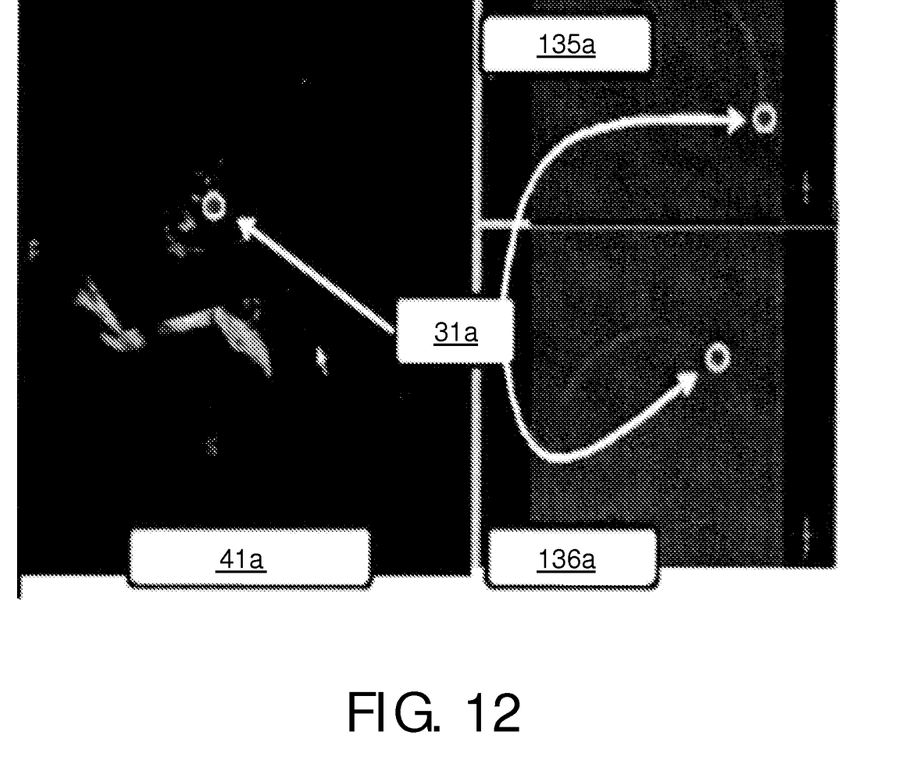
FIG. 12 illustrates an exemplary display of X-ray images and MPR images by the interventional tracking system of FIG. 10.

A stage S147 of flowchart 140 encompasses MPR imaging module 40a utilizing the 3D US real time coordinate location of catheter tip 31a as an origin of two or more MPR images. For example, as shown in FIG. 12, catheter tip 31a is identified in X-RAY images 135a and 136a, the 2D X-ray coordinates of catheter tip 31a are converted into 3D US real-time coordinate location of catheter tip 31a, and MPR images 41a are generated with the 3D US real-time coordinate location serving as the origin of MPR images 41a of catheter tip 31a.

Referring back to FIGS. 10 and 11, upon the first execution of stage S147, flowchart 140 may return to stages S141 and S143 to update the 3D US real-time coordinate location of catheter tip 31a and therefore update the MPR images. This allows for accurate tracking of catheter tip 31a as catheter 30a is navigated within cardiac anatomical region 91 and/or the ultrasound probe 20a is moved relative to cardiac anatomical region 91. Stages S141-S147 will cycle until the procedure is completed.

Figure 13:
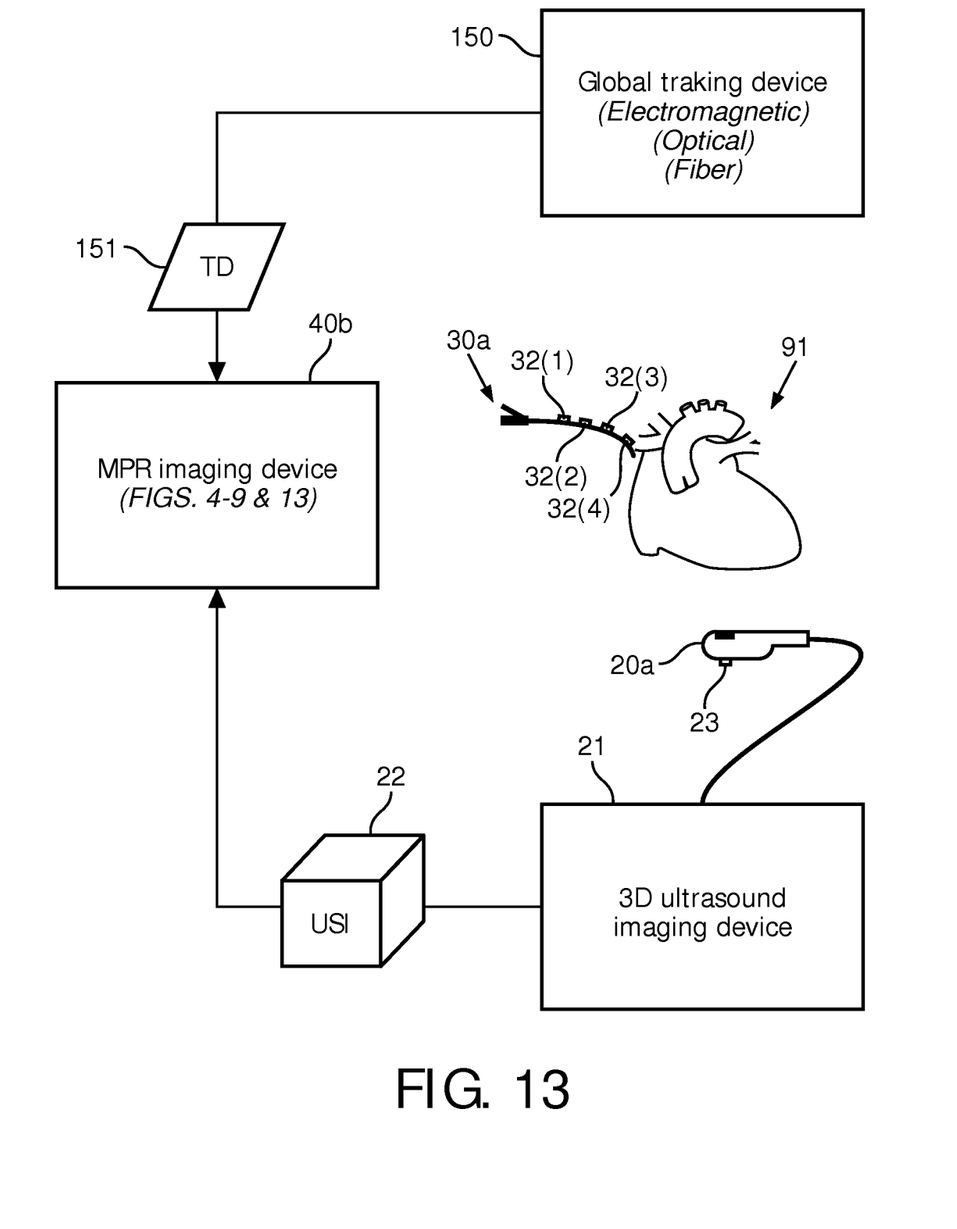
FIG. 13 illustrates a second exemplary embodiment of the interventional tracking system of FIG. 1.

FIG. 13 illustrates an interventional tracking system employing an embodiment of 3D US imaging system of FIG. 1, a tracking system and an embodiment of MPR imaging device 40 of FIG. 1.

For purposes of the present invention, the tracking system is broadly defined herein as any system including one or more position probe sensors 23 attached to ultrasound probe 20a, one or more position tool sensors 32(1)-(4) attached to catheter 30a and a global tracking device 150 structurally configured for tracking position sensors 23 and 32(1)-(4) within a global coordinate system. Examples of the tracking system include, but are not limited to, any type of electromagnetic tracking system, any type of optical tracking system, and any type of shape sensing system (e.g., optical fiber). In one embodiment, the Aurora™ Electromagnetic Tracking System commercially sold by NDI may serve as an electromagnetic tracking system.

In practice, position sensors 23 and 32(1)-(4) may have any required degrees of freedom ("DOF"), such as, for example, five (5) DOF or six (6) DOF.

Figure 14:
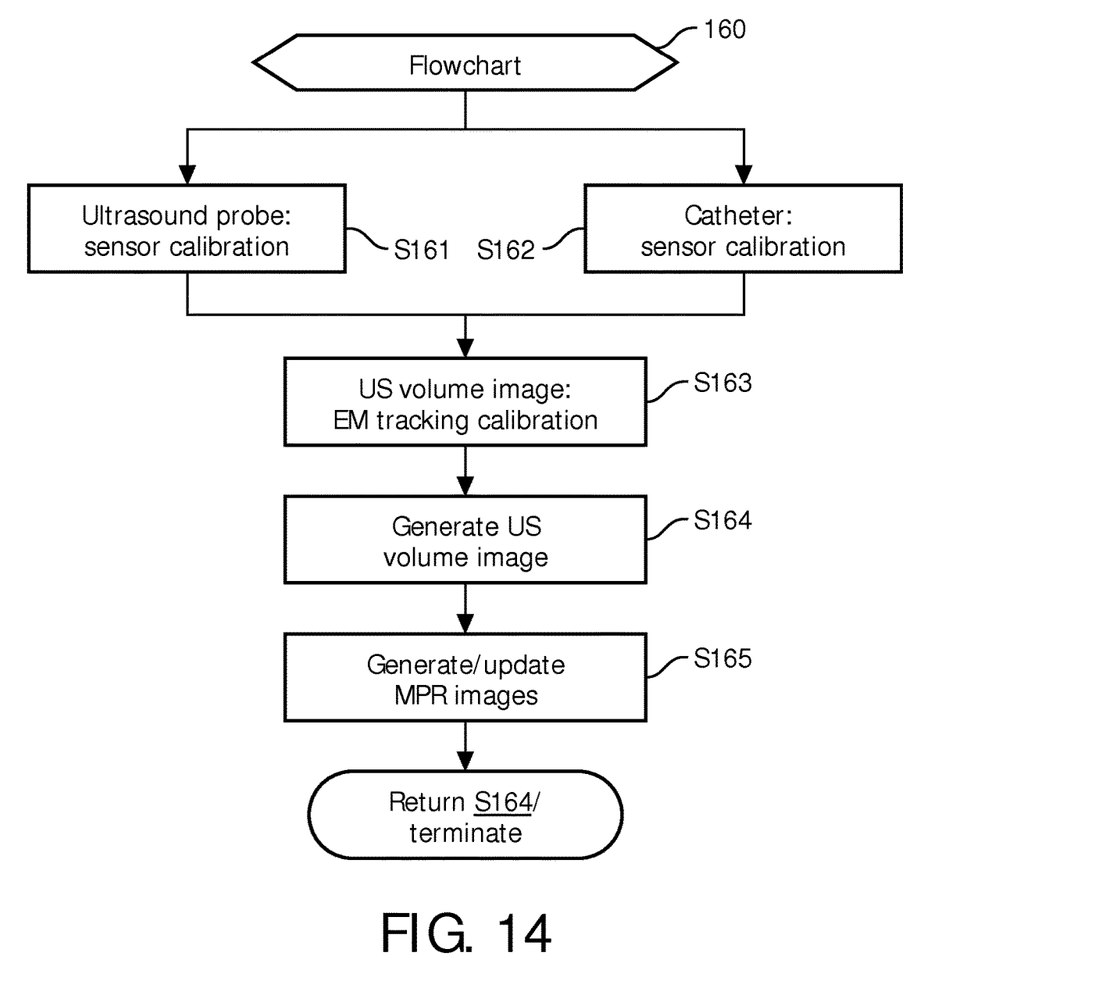
FIG. 14 illustrates a second exemplary embodiment of the interventional tracking method of FIG. 2.

In operation, an interventional tracking method represented by a flowchart 160 shown in FIG. 14 is executed for purposes of generating MPR images of a portion or an entirety of a catheter 30a within a cardiac anatomical region 91 as derived from an ultrasound volume image 22 and tracking of position sensor(s) 23 and 32 within a global coordinate system Specifically, referring to FIG. 14, a stage S161 of flowchart 160 encompasses a calibration of ultrasound probe 20a to a coordinate space of position tool sensor 23 as known in the art, and a stage S162 of flowchart 160 encompasses a calibration of catheter 30a to a coordinate space of each position probe sensor 32 as known in the art.

A stage S163 of flowchart 160 encompasses a registration of the calibrations to the global coordinate system as known in the art whereby the tip and body of catheter 30a may be registered to corresponding points in the ultrasound volume image 22.

A stage S164 of flowchart 160 encompasses a generation of ultrasound volume image 22 as catheter 30a is being introduced into and navigated within cardiac anatomical region 91.

A stage S165 of flowchart 160 encompasses a generation of MPR images based on the registration of the calibrations to the global coordinate system. More particularly, a tip of catheter 30a may be identified in the global coordinate system and thus in ultrasound volume image 22 whereby MPR images may be generated with the catheter tip serving as the origin, such as, for example, MPR images 73 and 74 shown in FIG. 6. Concurrently or alternatively, sensor 32 along the body of catheter 30a may be identified in the global coordinate system and thus in ultrasound volume image 22 whereby MPR images may be generated with the sensors 32 serving as origins, such as, for example, MPR images 82-84 shown in FIGS. 7-9. A warped ultrasound image volume may then be generated as previously described herein in connection with FIGS. 8 and 9.

Upon the first execution of stage S165, flowchart 140 may return to a cycle of stages S164-S165 to update the MPR images. This allows for accurate tracking of the catheter tip and body as catheter 30a is navigated within cardiac anatomical region 91 and/or the ultrasound probe 20a is moved relative to cardiac anatomical region 91. Stages S164-S165 will cycle until the procedure is completed.

In practice, only one position probe sensor 32 may be employed when exclusively tracking the tip of catheter 30a.

From the description of FIGS. 1-14, those having skill in the art will have a further appreciation on how to implement systems and methods of the present invention for any interventional procedure.

In practice, any number of X-ray imaging devices, 3D US imaging device and a MPR imaging module may be integrated into a single device.

While various exemplary embodiments of the present invention have been illustrated and described, it will be understood by those skilled in the art that the exemplary embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A system, comprising:
   an interventional tool having at least one image tracking point;
   an ultrasound imaging system including an ultrasound probe operable to generate an ultrasound volume image of at least a portion of the interventional tool within an anatomical region; and
   a multi-planar reformatting imaging module operable to generate at least two multi-planar reformatting images of the ultrasound volume image of the at least a portion of the interventional tool within the anatomical region, wherein a generation of the at least two multi-planar reformatting images includes:
   an identification of each image tracking point within the ultrasound volume image; and
   a utilization of each identified image tracking point as an origin of at least one of the least two multi-planar reformatting images.

2. The system of claim 1, wherein the interventional tool is a catheter.

3. The system of claim 1, wherein the imaging tracking point is located within a tip section of the interventional tool.

4. The system of claim 1, wherein the at least two multi-planar reformatting images are orthogonal.

5. The system of claim 1, wherein each multi-planar reformatting image has a fixed orientation within the ultrasound volume image.

6. The system of claim 1, wherein the multi-planar reformatting imaging module is further operable to dynamically update the least two multi-planar reformatting images as the interventional tool is navigated within the anatomical region.

7. The system of claim 1, wherein the multi-planar reformatting imaging module is further operable to dynamically update the least two multi-planar reformatting images as the ultrasound probe is moved relative to the anatomical region.

8. The system of claim 1, further comprising:
   an X-ray imaging system operable to generate at least two X-ray images of the at least a portion of the interventional tool within the anatomical region, wherein the identification of each imaging tracking point within the ultrasound volume image includes:
   an identification of each imaging tracking point within the at least two X-ray images; and
   a conversion of each identified imaging tracking point within the at least two X-ray images to the ultrasound volume image.

9. The system of claim 1, further comprising:
   a global tracking system including at least one tool sensor integrated with the interventional tool, wherein each tool sensor defines one of the at least one imaging tracking point.

10. The system of claim 9, wherein each tool sensor is an electromagnetic sensor.

11. The system of claim 9,
   wherein the global tracking system further includes at least one probe sensor integrated with the ultrasound probe; and
   wherein the identification of each imaging tracking point within the ultrasound volume image includes a co-registration of each tool sensor and each probe sensor to a global tracking coordinate system.

12. The system of claim 9, wherein the generation of the at least two multi-planar reformatting images includes:
   generating the at least two multi-planar reformatting images normal to the interventional tool relative to the tool sensors.

13. The system of claim 12, wherein the multi-planar reformatting imaging module is further operable to stack the at least two multi-planar reformatting images to form a warped ultrasound volume image relative to an axial alignment of the at least a portion of the interventional tool within the ultrasound volume image.

14. The system of claim 13, wherein the multi-planar reformatting imaging module is further operable to slice the warped ultrasound volume image into at least one additional multi-planar reformatting image to visualize the at least portion of the interventional tool and surrounding portions of the anatomical region.

15. The system of claim 13, further comprising:
an image modality operable to generate a scan image of the anatomical region,
   wherein the multi-planar reformatting imaging module is further operable for fusing the warped ultrasound volume image and the scan image.

16. A method, comprising:
navigating an interventional tool within an anatomical region, the interventional tool having at least one image tracking point;
an ultrasound probe generating an ultrasound volume image of at least a portion of the interventional tool within the anatomical region; and
a multi-planar reformatting imaging module generating at least two multi-planar reformatting images of the ultrasound volume image of the at least a portion of the interventional tool within the anatomical region, wherein the generation of the at least two multi-planar reformatting images includes:
   an identification of each image tracking point within the ultrasound volume image; and
   a utilization of each identified image tracking point as an origin of at least one of the least two multi-planar reformatting images.

17. The method of claim 16, further comprising:
an X-ray imaging system generating at least two X-ray images of the at least a portion of the interventional tool within the anatomical region, wherein the identification of each imaging tracking point within the ultrasound volume image includes:
   an identification of each imaging tracking point within the at least two X-ray images; and
   a conversion of each identified imaging tracking point within the at least two X-ray images to the ultrasound volume image.

18. The method of claim 16, further comprising:
a global tracking system including at least one tool sensor integrated with the interventional tool and at least one probe sensor integrated with the ultrasound probe,
   wherein each tool sensor defines one of the at least one imaging tracking point, and
   wherein the identification of each imaging tracking point within the ultrasound volume image includes a co-registration of the at least one tool sensor and the at least one probe sensor to a global tracking coordinate system.

19. The method of claim 16, further comprising:
a global tracking system including a plurality of tool sensors integrated with the interventional tool, wherein the generation of the at least two multi-planar reformatting images includes:
   generating the at least two multi-planar reformatting images normal to the interventional tool relative to the tool sensors; and
the multi-planar reformatting module stacking the least two multi-planar reformatting images to warp the ultrasound volume image relative to an axial alignment of the at least a portion of the interventional tool within the ultrasound volume image.

20. The method of claim 19, further comprising:
an image modality generating a scan image of the anatomical region,
   wherein the multi-planar reformatting imaging module fuses the warped ultrasound volume image and the scan image.

* * * * *